United States Patent [19]

Siler, Jr. et al.

[11] Patent Number: 4,827,557
[45] Date of Patent: May 9, 1989

[54] GOGGLE WIPER

[75] Inventors: Lawrence L. Siler, Jr., Lake Oswego; Richard A. Siler, Hillsboro, both of Oreg.

[73] Assignees: Sandra L. Siler, Lake Oswego; Sall J. Siler, Hillsboro, both of Oreg.; a part interest

[21] Appl. No.: 871,448

[22] Filed: Jun. 6, 1986

[51] Int. Cl.⁴ ............... G02C 13/00; A47L 25/00
[52] U.S. Cl. ........................... 15/245; 15/104 S; 280/813
[58] Field of Search .......... 15/104 S, 227, 236 R, 15/245, 250.36; 401/7, 8, 25, 27, 130, 139, 161; D32/41; 280/813, 816

[56] References Cited

U.S. PATENT DOCUMENTS 3,351,969 11/1967 Cline ..................... 15/245
4,342,128 8/1982 Doyle ..................... 15/245

Primary Examiner—Edward L. Roberts
Attorney, Agent, or Firm—Jack E. Day

[57] ABSTRACT

A wiper for ski goggles is provided. The wiper is adapted to be removably mounted on a mounting member having a longitudinal axis. The wiper has a first and second end, with one end having a single-edged blade contoured to fit the surface of ski goggles and a second end having a holder for mounting on a mounting member.

4 Claims, 1 Drawing Sheet

GOGGLE WIPER

The present invention, generally, is a wiper to remove snow from goggles and, more specifically, is a fixture including a wiper means to be fastened onto a user's thumb, wrist, ski pole, or the like, so that the user can easily remove, from his or her ski goggles or other vision protection devices, snow and other undesireable matter that would tend to obscure vision.

BACKGROUND OF THE INVENTION

Skiers and other snow sports enthusiasts are constantly vexed by the problem presented by snow, sleet, freezing rain, slush and other objectionable matter collecting on their goggles during use, and by the need to remove this matter promptly, without stopping their activity. This problem is especially irritating when snow is wet and sticky. Not doing something about it immediately upon perception of the problem exposes skiers to the real danger of injury, to themselves and others. Many skiers give up the battle and don't wear goggles, or push them onto their foreheads or hats where they provide no protection. Others use their sleeves, the back of their hands or gloves, kerchiefs, etc., to try and keep their goggles clean during sking. However, none of these efforts is particularly effective or satisfactory, and few efforts, if any, have been made to solve the specific problem.

Needed is a means of removing snow from ski goggles which can be easily and conveniently carried, which doesn't interefere with a skier's mobility when not needed, and which is available for use immediately upon perception that the goggles need to be cleaned, and without any complex procedure or thought required, if possible.

There is little prior art relating to utensils for the removal of foreign material from glass and other fragile materials, such as the plastics used in ski goggles and glasses, which can also be easily carried until needed, and then used with a minimum of delay and effort.

Of course, the problem of cleaning unwanted matter from various objects and surfaces has long been recognized, and there are at least as many solutions to the problem as there are types of objects to clean. It is instructive to examine some of the proposed solutions to these problems in order to appreciate the solution represented by the present invention.

Luttinger U.S. Pat. No. Des. 55,290 discloses a design for a cleaner for carbide lamps.

The following U.S. patents all disclose scrapers or wipers for cleaning kitchen utensils and dishes:
Norton U.S. Pat. No. Des. 26,798
Hoffman U.S. Pat. No. Des. 34,727
Schwartz U.S. Pat. No. Des. 163,774
Lower U.S. Pat. No. 2,380,855
Peterson U.S. Pat. No. Des. 199,962 and U.S. utility Pat. No. 3,178,747 disclose a shaped flexible multi-purpose scraper or wiper.

Other patents discloses various designs for wipers or scrapers to remove ice, mud and/or dirt from various items and places:
Crossman U.S. Pat. No. Des. 27,141—wheels;
Baldwin U.S. Pat. No. Des. 193,679—golf balls;
Young U.S. Pat. No. Des. 269,944—gasoline nozzle.

The uses of some of these scrapers are only distantly related to the use herein dealt with. However, it is significant that although most of them incorporate holes for inserting fingers to help hold the tool during use, not one of them suggesst, or even infers, the possibility of fastening the scraper or wiper semi-permanently on the hand, wrist or on another tool used in the procedure associated with the cleaning process, during the time that the scraper or wiper might be needed.

Of course, everyone is acquainted with windshield wipers and the squeegee tools used to clean windows. The efforts of inventors to adapt such devices to eyewear has long been a subject for cartoons. Nevertheless little, if anything, appears in the literature about such tools which could be easily carried when not needed, but instantly available for cleaning glasses and goggles when needed.

None of the above even addresses the problems solved by the present invention, which is to have conveniently available, for use whenever it is needed, an easily used means of removing, from ski goggles and the like, snow, slush, sleet, ice, rain, and other matter which would interfere with the skier's vision during skiing.

BRIEF DESCRIPTION OF THE PRESENT INVENTION

The present invention is a novel scraper or wiper, to be attached to a mounting member, which can be a thumb, wrist, glove, ski pole or the like of a skier, for the purpose of wiping snow, slush, sleet, ice, rain (frozen or otherwise), and other material from the glasses or goggles of such persons which might interfere with their vision when engaged in skiing, sledding, tobagganing, and the like activities.

The present invention includes a scraper or wiper means which is fabricated of a pliable soft rubber and which is for the purpose of wiping offending matter from the surface of goggles, without damaging their surface.

At the base of the wiper means is a holder means, which can be a circular band or a flexible strip with fastener means thereon, for the purpose of fastening the wiper on a mounting member, which can be a thumb or wrist (directly or over clothing, and with or without gloves), or around the top of a ski pole, so that when the user feels the need to wipe the undesired matter away, he simply raises the wiper up and gives the surface of the goggles one or more swipes to accomplish the purpose.

The present invention has several unexpected advantages:
it is easy to use;
it is always ready for use when needed;
the user doesn't have to stop his activities to use it;
it doesn't need to be withdrawn from a pocket to use;
it doesn't have to be examined to make sure that the blade is oriented properly;
its small size will not interfere with the skier's normal activities;
its lower weight will not fatigue the user;
being made of flexible rubber, it poses little danger if the user falls upon it or inadvertently jabs it towards his eyes;
it represents no great loss if mislaid, lost, stolen or destroyed.

These advantages will become apparent from the description which follows, taken in conjunction with the accompanying drawings.

DETAILED DESCRIPTION OF THE PRESENT INVENTION

Figure 1:
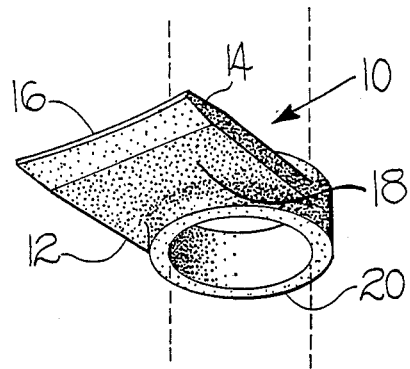
FIG. 1 discloses an isometric view of one embodiment of the present invention, with a holder means thereon for slipping over the thumb or ski-pole of a user.

The present invention 10, as disclosed in FIG. 1, includes a wiper means 12, composed of a semi-soft, flexible rubber blade 14 having a wiping edge 16 thereon, body 18, and holder means 20. Holder means 20 is intended to be mounted on a mounting member, which can be the thumb of a skier, or the end of a ski-pole.

In use, holder means 20 is slipped over the thumb, for example, after the skier is ready to start skiing, and is adjusted thereon so that, when the hand is raised to the face, the wiping edge 16 of blade 14 contacts the surface of the goggles.

The wiping edge 16 can have a curve therein which is complementary to the curved surface of the ski goggles, as shown.

The size of wiper means 12, and its extension from the skier's hand, are small enough to offer little or no interference with the skier's normal actions. If it is snowing, or if the skier has brushed against a tree laden with snow, so that his goggles become covered with snow and his vision is impaired, all he has to do is brush wiper means 12 across his goggles and his vision is restored. His brushing movement is similar to the normal gesture of wiping one's hand or sleeve across one's eyes so that it can easily become habitual.

Figure 2:
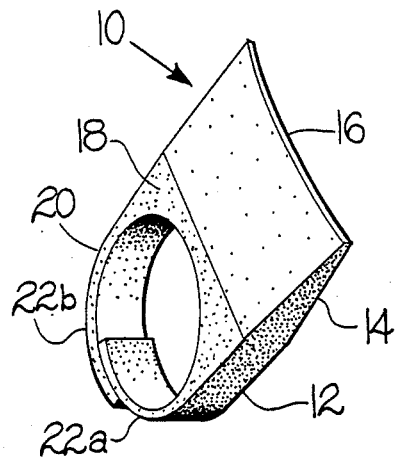
FIG. 2 discloses an isometric view of another embodiment of the present invention, with a holder means thereon for fastening the invention on the wrist of a user.

The same is true of the embodiment intended to fasten to the skier's wrist, disclosed in FIG. 2. This embodiment has much the same form and shape as that disclosed in FIG. 1, except it is slightly larger and the holder means 20 includes a pair of straps 22a and 22b having snaps, Velcro or the like thereon for affixing this embodiment snugly to the skier's wrist.

Figure 3:
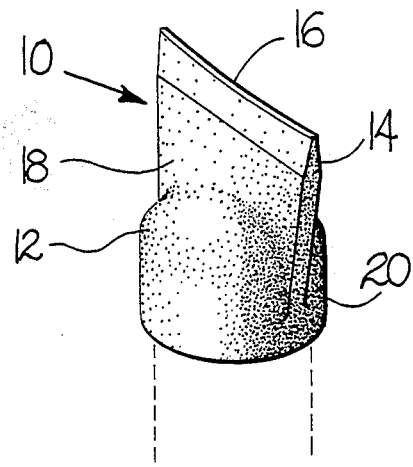
FIG. 3 discloses another embodiment for fastening on the handle end of a ski pole.

For the ski pole mounting, holder means 20 can have any of several configurations, including cup-like fastener means 24, as disclosed in FIG. 3, which slips over the end of the ski-pole. It will be apparent that this embodiment might pose a hazard to the skier's eye if the ski pole should encounter an obstacle just at the moment of use.

It will be seen that blade 14 of the wiper means is affixed more-or-less transversely to the axis of the thumb, wrist or ski pole. Especially for the thumb or wrist, this orientation permits the desired wiping motion which is the most natural for the skier.

It will be apparent to those skilled in the art that this invention could take many forms or embodiments without departing thereby from its spirit or intent. For example, the edge of the wiper blade, which has been shown as having a complementary curve to match the curve of the goggle surfaces, could be straight, without affecting substantially the effectiveness of snow removal. Gloves, mittens, cuffs or sleeves could have specially adapted mounting fixtures tailored thereto, for holding wiper means 12. Ski poles could be fabricated so that the holder means could be inserted like a cork in the handle end.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limted only by the claims which follow.

What we claim as our invention is:

1. A wiper for removing vision-obstructing matter from the transparent surface of ski goggles and the like, said wiper for removably mounting on a mounting member having a longitudinal axis, comprising:
   a. a substantially planar body means, said body means:
      1. being fabricated of a soft flexible material; and
      2. being substantially normal to said axis;
      3. having a first end and a second end:
         A. said first end having thereon a single-edged blade, said blade:
            I. lying in the plane of said body;
            II. being contoured to fit said transparent surface of said ski goggles; and
            III. being spaced from said axis and transverse thereto; and
         B. said second end having therein holder means for removably fitting over said mounting member.

2. A wiper for removing vision-obstructing matter from the transparent surface of ski goggles and the like, said wiper for removably mounting on a mounting member having a longitudinal axis, comprising:
   a. a substantially planar body means, said body means:
      1. being fabricated of a soft flexible material; and
      2. being substantially normal to said axis;
      3. having a first end and a second end:
         A. said first end having thereon a single-edged blade, said blade:
            I. lying in the plane of said body;
            II. being contoured to fit said transparent surface of said ski goggles; and
            III. being spaced from said axis and transverse thereto; and
         B. said second end having therein a loop for removably fitting over a wearer's thumb.

3. A wiper for removing vision-obstructing matter from the transparent surface of ski goggles and the like, said wiper for removably mounting on a mounting member having a longitudinal axis, comprising:
   a. a substantially planar body means, said body means:
      1. being fabricated of a soft flexible material; and
      2. being substantially normal to said axis;
      3. having a first end and a second end:
         A. said first end having thereon a single-edged blade, said blade:
            I. lying in the plane of said body;
            II. being contoured to fit said transparent surface of said ski goggles; and
            III. being spaced from said axis and transverse thereto; and
         B. said second end having therein a loop for removably fitting over a wearer's wrist.

4. The wiper means of claim 3, wherein said loop fitting over said wrist is comprised of straps having fasteners on the ends thereof.

* * * * *